US011198037B2

(12) United States Patent
Volterrani et al.

(10) Patent No.: US 11,198,037 B2
(45) Date of Patent: Dec. 14, 2021

(54) INDIVIDUALLY TAILORED EXERCISE TRAINING AND REHABILITATION TECHNIQUE: MEDICAL PERSONAL TRAINER

(71) Applicant: IRCCS San Raffaele Roma S.r.l., Rome (IT)

(72) Inventors: Maurizio Volterrani, Rome (IT); Ferdinando Iellamo, Rome (IT); Cristiano Maria Verrelli, Rome (IT); Marco Tiberti, Rome (IT); Patrizio Tomei, Rome (IT)

(73) Assignee: IRCCS San Raffaele Roma S.r.l., Rome (IT)

( * ) Notice: Subject to any disclaimer, the term of this patent is extended or adjusted under 35 U.S.C. 154(b) by 81 days.

(21) Appl. No.: 16/324,582

(22) PCT Filed: Aug. 4, 2017

(86) PCT No.: PCT/IT2017/000165
§ 371 (c)(1),
(2) Date: Feb. 11, 2019

(87) PCT Pub. No.: WO2007/099206
PCT Pub. Date: Sep. 7, 2007

(65) Prior Publication Data
US 2019/0175988 A1    Jun. 13, 2019

(30) Foreign Application Priority Data
Aug. 9, 2016  (IT) .................. 102016000083609

(51) Int. Cl.
*A63B 24/00*    (2006.01)
*A61B 5/024*    (2006.01)
(Continued)

(52) U.S. Cl.
CPC .......... *A63B 24/0075* (2013.01); *A61B 5/024* (2013.01); *A61B 5/02405* (2013.01);
(Continued)

(58) Field of Classification Search
CPC ............ A63B 24/0075; A63B 24/0087; A63B 24/0062; A63B 22/02; A63B 22/0605;
(Continued)

(56) References Cited

U.S. PATENT DOCUMENTS

2009/0069156 A1\* 3/2009 Kurunmaki ........ A63B 24/0062
482/9
2011/0207110 A1  8/2011 Huovinen
(Continued)

FOREIGN PATENT DOCUMENTS

WO   WO 2007/099206   9/2007
WO   WO 2018/029717   2/2018

OTHER PUBLICATIONS

International Search Report and the Written Opinion dated Feb. 26, 2018 From the International Searching Authority Re. Application No. PCT/IT2017/000165. (12 Pages).
(Continued)

Primary Examiner — Sundhara M Ganesan
Assistant Examiner — Shila Jalalzadeh Abyaneh (57) ABSTRACT

The present invention concerns a new individually tailored exercise training and rehabilitation technique, referred to as "MPT: Medical Personal Trainer". More precisely, the invention concerns an innovative method to be used in the field of physical activity and exercise training/rehabilitation programs for healthy individuals and for patients with chronic diseases. It merges together, in an interactive way, advanced notions from medicine, engineering, mathematics, artificial intelligence, in order to provide new clinical perspectives for automatic personalized health care as well as
(Continued)

novel insights on individually-tailored management and advanced treatment, in a user-familiar setting, of healthy subjects (including elderly) and patients with chronic diseases.

9 Claims, 3 Drawing Sheets

(51) Int. Cl.
*G16H 20/30* (2018.01)
*A63B 22/02* (2006.01)
*A63B 22/06* (2006.01)
*G16H 40/63* (2018.01)
*G16H 15/00* (2018.01)

(52) U.S. Cl.
CPC .......... *A63B 22/02* (2013.01); *A63B 22/0605* (2013.01); *A63B 24/0062* (2013.01); *A63B 24/0087* (2013.01); *G16H 15/00* (2018.01); *G16H 20/30* (2018.01); *G16H 40/63* (2018.01); *A63B 2024/0078* (2013.01); *A63B 2024/0093* (2013.01); *A63B 2230/045* (2013.01); *A63B 2230/067* (2013.01)

(58) Field of Classification Search
CPC ...... A63B 2024/0078; A63B 2230/045; A63B 2230/067; A63B 2024/0093; A61B 5/024; A61B 5/02405; G16H 40/63; G16H 15/00; G16H 20/30
See application file for complete search history.

(56) References Cited

U.S. PATENT DOCUMENTS

2015/0217164 A1    8/2015  Lagree
2017/0216672 A1*   8/2017  Wisbey ................ A61B 5/6815

OTHER PUBLICATIONS

Rapporto di Ricerca e Opinione Scritta [Search Report and Written Opinion] dated Apr. 7, 2017 From the Ministero dello Sviluppo Economico, Direzione Generale Sviluppo Produttivo e Competitivita Uffico Italiano Brevetti e Marchi Re. Application No. IT201600083609. (8 Pages).
Kiviniemi et al. "Endurance training guided individually by daily heart rate variability nteasurentents",European Journal of Applied Physiology, 101(6):743-751, Dec. 2007.
Manzi et al. "Relation Between Individualized Training Impulses and Performance in Distance Runners", Official Journal of the American College of Sports Medicine, 41(11): 2090-2096, 2009.
Paradiso et al. "Experimental Heart Rate Regulation in Cycle-Ergometer Exercises", IEEE—Transactions On Biomedical Engineering 60 (1): 135-139, 2013.

* cited by examiner

INDIVIDUALLY TAILORED EXERCISE TRAINING AND REHABILITATION TECHNIQUE: MEDICAL PERSONAL TRAINER

RELATED APPLICATIONS

This application is a National Phase of PCT Patent Application No. PCT/IT2017/000165 having International filing date of Aug. 4, 2017, which claims the benefit of priority of Italian Patent Application No. 102016000083609 filed on Aug. 9, 2016. The contents of the above applications are all incorporated by reference as if fully set forth herein in their entirety.

FIELD AND BACKGROUND OF THE INVENTION

The present invention concerns a new individually tailored exercise training and rehabilitation technique, referred to as "MPT: Medical Personal Trainer". More precisely, the invention concerns an innovative method to be used in the field of physical activity and exercise training/rehabilitation programs for healthy individuals and for patients with chronic diseases. It merges together, in an interactive way, advanced notions from medicine, engineering, mathematics, artificial intelligence, in order to provide new clinical perspectives for automatic personalized health care as well as novel insights on individually-tailored management and advanced treatment, in a user-familiar setting, of healthy subjects (including elderly) and patients with chronic diseases.

Benefits of Physical Activity

The health benefits of regular exercise and physical activity are hard to be ignored. Exercise can help prevent excess weight gain or help maintain weight loss. Being active boosts high-density lipoprotein (HDL) cholesterol and decreases unhealthy triglycerides, while keeping the blood flowing smoothly with a decrease of risk of cardiovascular diseases. Regular physical activity can improve muscle strength and boost endurance while delivering oxygen and nutrients to tissues and helping the cardiovascular system to work more efficiently. People who are insufficiently physically active have a 20%-30% increased risk of all-cause mortality compared to those who engage in at least 30 minutes of moderate intensity physical activity on most days of the week. In particular, approximately 3.2 million deaths each year are attributable to insufficient physical activity. Participation in 150 minutes of moderate physical activity each week is estimated to reduce the risk of ischemic heart disease by approximately 30%, the risk of diabetes by 27% and the risk of breast and colon cancer by 21%-25%. Furthermore, the level of insufficient physical activity is directly related to the level of country income: the increased automation of work and other aspects in life in higher-income countries is a likely determinant of such a relationship. Awareness and education about this keeps on further increasing: even consumers that have shied away from the traditional gyms are getting their groove back in boutique workout studios, outdoor boot camps and even some online do-it-yourself programs. Traditional exercises are being transformed into specialties and new programs are being designed and developed at a breakneck pace. On the other hand, the increasingly aging population with the prevalence of chronic diseases (such as, for instance, Chronic Heart Failure, Parkinson's disease, Rheumatoid Arthritis) and rising costs have brought about some unique and rising healthcare challenges to our global society, moving towards the definition of advanced automatic training/rehabilitation programs to be performed in a user-familiar setting.

The Optimal Dose of Exercise

It is envisaged that by treating patients through a personalized approach, healthcare will be more cost-effective and sustainable. However, the admissible "optimal" dose of exercise, defined in terms of volume and intensity of exercise, required in order to achieve improvements in aerobic fitness, metabolic control and prognostic indicators, still remains a crucial unanswered issue. Defining the admissible optimal dose of exercise to safely maximize health outcomes (i.e. how much exercise training is enough, and not too much or too low) is now considered a priority ([7], [9], [11]).

Determining and administering the admissible "safe and effective" dose of exercise turns out to be not only crucial for healthy subjects to maximize health outcomes but also and especially for patients with chronic diseases. The authors of the present invention have recently reported—in marathon runners as well as in patients with chronic heart failure—that exercise training programs simply guided by the TRIMPi (individualized training impulses) method—a measure of the internal training load which integrates in a single term both the volume and intensity effects of exercise—induced a dose-dependent curvilinear response in several parameters exploring ANS (Autonomic Nervous System) cardiac regulation, as assessed at rest ([4], [5]). Indeed, despite a prominent plasticity of cardiac autonomic regulation, there is a point on the dose-response curve between TRIMPi-based training load and ANS regulation after which an increase in training load does not induce a substantial increase in functional capacity and could be even detrimental in specific patients' population ([4]). The benefit of increasing exercise performance by increasing the individually computed training load from moderate to higher doses of exercise is thus to be actually weighted against the lack of an improvement in cardiac vagal modulation and against the possible increase of the risk of adverse (cardiac) events [especially in patients with chronic heart failure].

Limitations of Guidelines for Training and Rehabilitation Exercises

The mean Heart Rate (HR) is typically used as a measure of the exercise intensity during training/rehabilitation exercises. Current guidelines for exercise training in both healthy individuals and ill patients are targeted to percentages of maximal Heart Rate (MHR) or HR Reserve (HRR) values, the latter being monitored through wearable heart rate monitors (even in the hospital setting for patients affected by chronic heart failures).

In this regard, it needs to be recognized and outlined that exercise training programs based solely on percentage of MHR or on HRR are likely to impose variable internal load at individual level. Subjects exercising at, for example, 40-70% HRR may be working at individually different relative intensities. According to this concept, it has been observed a wide inter-subjects variability in lactate response (e.g., an indicator of internal load) in individuals with similar aerobic capacity while exercising at the same percentage of VO2max (e.g., an indicator of energy expenditure). In addition, HR is under sympathetic and parasympathetic control, the main determinants of HR both at rest and during exercise, and this cannot be discerned by simple analysis of crude HR. This limitation is further enhanced in patients with cardiac diseases, e.g. patients with chronic heart failure, because of chronotropic incompetence and beta-blockers treatment. This concept is in agreement with the current general consensus that exercise training should be individually tailored to the patient's clinical and functional status ([7, 9]). In addition, recent finding indicate that the training HR might depend upon molecular changes of the Sino Atrial (SA) node, supporting the hypothesis that training might affect HR in a more complex fashion than usually considered (see [3]).

Hence, a key question still persists: it regards the determination of the admissible "safe and effective dose" of exercise (in terms of a suitable HR reference signal) to be automatically prescribed to the user even in a (user-familiar) non-hospital setting, on an individual and exercise moment-contingent basis.

The Role of HRV at Rest

As previously mentioned, cardiovascular responses to acute and chronic exercise are mainly determined by acute changes and adaptations in autonomic nervous system (ANS) control, namely by modifications in sympathetic and parasympathetic activity to the cardiovascular system, that could be detected and monitored by non-invasive methodologies.

In this context, analysis of HRV at rest could be realistically effective in assisting exercise training programs, in addition to monitoring the training status [12]. This approach might also respond to the increased demands of information generated by the widespread use of wearable personal heart rate monitors ([1]), thus appealing to a vast population of active individuals. A typical aspect of exercise training regards the progressive changes in ANS cardiac regulation (assessed at rest) that are linked to the dose of the previously performed exercise, on an individual basis. This naturally leads to the use of HRV-at-rest-derived indices of ANS functioning to plan a physical activity program on the basis of longitudinal resting assessments relying on daily changes in the low frequency (LF) and high frequency (HF) spectral components of HRV, taken as indices of sympathetic ad parasympathetic cardiac modulation, respectively (see for instance [6]). However, neural cardiac modulation during an exercise session (composed of several phases) can vary due to several factors, both external (e.g., environmental) and internal (e.g., psychological and physical status), that cannot be predicted by resting assessments.

Some Prior Art Systems

US 2015/0217164 A1 [13] concerns pilates exercise routine system and method. Due to a number of possible configurations of pilates machines, the document proposes to download a user profile in each machine from a cloud or other storage, so that the exercise machine knows the history for the user and can automatically accordingly adjust the settings of the exercise machine. Moreover, performance data may be included, e.g. the date, the duration of the exercises performed, the workout intensity level, blood pressure, pulse, heart rate, respiration, energy output, special adjustments to the apparatus as well as any other information that may be useful in measuring a member's fitness or performance level.

WO2007/099206 A1 [14] concerns a method and system for controlling a training plan for a user having a chosen aim for training, where: i) at least one parameter describing physical characteristics of the user is determined; ii) a training plan consists of plurality of days, with each day having one or more training sessions or rest; iii) each performed and coming session has a training load described by one or more parameters; iv) a training template is determined according to the given aim and to additional parameters describing physical characteristics, with each training template having a cumulative training load target according to the aforesaid parameter and to the chosen aim and consisting of one or more training sessions or rest in each day and with each training session of the template having a pre-selected training load; v) an adapting window is determined, with the adapting window consisting of a plurality of days that include one or more previous sessions and one or more coming sessions according to the training template; vi) training loads of each session in the adapting window are combined into a cumulative training load that is compared to the cumulative training load target in the template; vii) depending on the comparison, one or more coming sessions in the adapting window are adapted by changing one or more training loads among these, so that the performed training load and the training load of the coming sessions as a combination meet the cumulative training load target. Particularly this last document presents an accurate connection between the exercise parameters (intensity, duration) and the accumulated body fatigue effect (scaled in terms of a physiological quantity, preferably EPOC, i.e. excess-post-exercise oxygen consumption [oxygen ml/body weight kg]). Training level can be thus increased or decreased, depending on the criteria required for each training level such as: training frequency, training load, TRIMP, HRV, activity class, time spent in the current training level. Anyway, both the documents above, do not rely, to successfully adjust the effort, on the on-line short term evaluated (on-the-fly) HRV, whose indices are meaningfully computed during each controlled phase of the exercise at constant HR. Such on-the-fly HRV indices are the ones which capture a neural cardiac modulation actually varying along the exercise phases due to both external (e.g., environmental) and internal (e.g., psychological and physical status) factors and thus reflecting such external and internal conditions for the specific user on the exercise-moment-contingent basis.

Underlying Motivating Technology by the Authors

In recent theoretical/experimental studies [8] and [10] by the Inventors, it is showed that it is possible to construct technologically advanced cycle-ergometers/treadmills which are able to automatically adjust the load/speed, respectively, in order to precisely regulate the HR of a healthy subject to a given reference constant value HR*.

This is done by feeding back (and by letting it be processed by an advanced learning control) the measured HR, without knowing the parameters of the system which depend on both the specific exerciser and his actual specific conditions. On the other hand, as reported in [8], there is evidence in the literature ([2] and related papers by the same authors) that a large decrease of a certain HRV index (the LF/HF ratio) appears when passing from the sub-ventilatory threshold to the supra-ventilatory one. Time is ripe to effectively consider the need of performing a technologically advanced regular physical activity outside medically-supervised settings, as a crucial issue for healthy subjects and patients, with the physiological processes related to the attendant changes in the individual physical capacity over the time of the exercise being to be specifically taken into account.

SUMMARY OF THE INVENTION

It is therefore an aim of the present invention the one of realizing an individually tailored exercise training and rehabilitation apparatus and method allowing for overcoming the limits of the solutions according to the prior art and achieving the described technical results.

A further aim of the invention is that said apparatus can be realized with substantially limited costs, as far as both the construction and the operative costs are concerned.

Not last aim of the invention is the one of realizing an individually tailored exercise training and rehabilitation apparatus being substantially simple, safe and reliable.

It is therefore subject-matter of the invention methods and tools for solving the above-mentioned problems of the prior art, as stated in the appended claims, which form integral part of the present description.

BRIEF DESCRIPTION OF THE SEVERAL VIEW OF THE DRAWINGS

The invention will be disclosed herein below for illustrative, but non-limitative purposes, according to preferred embodiments thereof, with reference in particular to the following embodiments, wherein an embodiment is also illustrated by.

DESCRIPTION OF SPECIFIC EMBODIMENTS OF THE INVENTION

The objective of the invention is thus the introduction of a new, integrated, cost-effective, completely automated, individually-tailored exercise training or rehabilitation technique. The exercise session is divided into N different, subsequent session phases at constant HR.

No continuously invasive techniques or expensive and complex indirect methods will be used during the exercise to maintain the admissible (safe and effective) nature of the exercise. Only the (short term evaluated) HRV on-line monitored during each constant-HR-controlled phase of the exercise and the TRIMP or TRIMPi indices will guide the personalized determination of the feedback-based definition of the sequence of reference HR to be provided at each phase.

Prerequisites
1. An inner control loop, which is able to maintain the HR of the subject/patient close to (within 5%, preferably within 3%) a given piecewise-constant HR reference signal, is available (see [8] and [10] concerning training/rehabilitation machines like cycle-ergometers or treadmills as traces which show that the set of such choices is not empty).
2. A device providing the heart beats time instants is available (an example is disclosed in [8] and [10]).
3. The parameters (including maximal HR and HR at rest as well as, when possible, a preliminarily determined lactate profile for both healthy subjects and patients) involved in the determination of the TRIMP or TRIMPi indices for each subject (an example of determination of such indexes is disclosed in [12], here integrally included by reference) are available, along with a related individual or set-uniform cumulative threshold (referred without loss of generality to as $S_{\Sigma, TRIMPi}$ and taking into account the whole exercise composed by phases at constant HR) for each user or each set $\Sigma$ of healthy subjects or patients with a specific disease.
4. The relationships between on-the-fly HRV (i.e. on-line evaluated HRV) and the type of the exercise are defined in terms of an individual or set-uniform threshold (referred without loss of generality to as $S_{\Sigma, HRV}$) identifying admissible (HRV index larger than $S_{\Sigma, HRV}$) and non-admissible (HRV index smaller than or equal to $S_{\Sigma, HRV}$) exercises for each user or each set $\Sigma$ of healthy subjects or patients with a specific disease (consider [8] concerning LF/HF in healthy subjects—with $S_{\Sigma, HRV}=1$—as a trace showing that the set of such choices is not empty). HRV indices and related threshold $S_{\Sigma, HRV}$ are intended to be compatible in terms of acquisition/computation methods.

The thresholds in 3. and 4. can be generally established through a preliminary phase at incremental controlled HRs by simultaneously monitoring HRV and fatigue evaluation indices for the specific user with the instrumentation for gas exchange or lactate data analysis being possibly used. A complete database of on-line signals can be accordingly constructed for once, including the short term evaluated HRV indices referring to phases at constant controlled HR. On the basis of the overall data collected in this phase, the relationships between (short term evaluated) HRV indices during exercise and exercise exertion can be preliminarily determined, as well as the admissible dose of exercise in terms of TRIMP/TRIMPi.

Outcome:

A user-friendly, safe and effective, integrated algorithm which automatically assigns HR reference values to each specific subject/patient during the training/rehabilitation exercise, on the individual and moment-contingent basis by innovatively handling the on-line (short term evaluated) HRV- and TRIMP- or TRIMPi-formulas and with no use of continuously invasive techniques and/or expensive and complex indirect methods during the exercise. The crucial drawbacks of previous related approaches are ingeniously eliminated: the on-line HRV-feedback, as an index of neural cardiac modulation during each constant-HR-controlled exercise phase, batch-continuously modifies the sequence of HR references, with the TRIMP or TRIMPi quantities to provide an initial increasing sequence of HR references and to simultaneously quantify the possible modification of such HR reference values.

Detailed Self-Contained Technical Description of the Algorithm

Preliminaries

The TRainingIMPulse (TRIMP) Method, introduced by Banister et al. (see [12]), for the i-subject relies on the definition of the following real-valued function:

$$TRIMP(T) = T H R_{n,m,i} B e^{C H R_{n,m,i}} \quad (1)$$

in which T (here expressed in minutes without loss of generality and not depending on the i-subject for the sake of simplicity and compactness) is the duration of the exercise (here assumed to be composed of one single phase in our terminology), while the normalized mean HR ("n" stands for "normalized"):

$$HR_{n,m,i} = \frac{HR_{m,i} - HR_{rest,i}}{HR_{maximal,i} - HR_{rest,i}}$$

relies on the mean HR $HR_{m,i}$ ("m" stands for "mean") which is monitored during the exercise for the i-th subject/patient/ individual. The constant positive values B and C in (1) are taken equal over the healthy subjects/patients set while $HR_{rest,i}$ and $HR_{maximal,i}$ are defined for the specific i-th subject/patient. Examples of values of B and C are given in [12]. Notice that the TRIMP(T) value in (1) can be interpreted as $$\int_0^T ITRIMP d\tau$$

wherein:

$$ITRIMP = \frac{TRIMP(T)}{T} \quad (2)$$

denotes the incremental TRIMP. On the other hand, the constant TRIMP in (1) can be extended in two directions:
  making B and C dependent on the specific i-subject/patient (namely $B_i$ and $C_i$);
  using n distinct HR-measurements over the exercise duration time window in place of the mean HR $HR_{m,i}$ in (1).
In this regard, let $$t_0, t_1, \ldots, t_n$$

be a sequence of time instants $t_j$ which a HR measurement corresponds to. Let us set, for the sake of simplicity, $t_0=0$ and $t_j-t_{j-1}=T/n$ (j=1, 2, . . . , n). We have:

$$HR_{n,i}(t_j) = \frac{HR_i(t_j) - HR_{rest,i}}{HR_{maximal,i} - HR_{rest,i}}$$

which leads to the definition of the ITRIMPi at the time instant $t_j$ for the specific i-subject/patient:

$$ITRIMPi(t_j) = HR_{n,i}(t_j) B_i e^{C_i HR_{n,i}(t_j)} \quad (3)$$

Consequently, the integral over [0,T] can be approximated by the lower integral sum $$TRIMPi(T) \cong \sum_{j=0}^{n-1} ITRIMPi(t_j) \frac{T}{n} \quad (4)$$

which (excepting for the use of a different normalization constant) leads to the definition of the TRIMPi in [5]:

$$TRIMPi(T) \doteq \frac{T}{n} \sum_{j=0}^{n-1} HR_{n,i}(t_j) B_i e^{C_i HR_{n,i}(t_j)} \quad (5)$$

It is clear that, when the $HR_{n,i}(t_j)$ are all equal to $HR_{n,m,i}$ and $B_i$, $C_i$ are all equal for each element of the set of individuals, (5) trivially reduces to (1).

Innovative General Algorithm MPT

Besides the first time sequence $t_0, t_1, \ldots, t_n$, taking values in the phase interval, consider a second time sequence (denoting different phases of the exercise):

$$T_0, T_1, \ldots, T_N$$

wherein:

$$T_l = l4 \text{ min}$$

with l=0,1, . . . , N, i.e.

$$T_0 = 0 \text{ min}$$
$$T_1 = 4 \text{ min}$$
$$T_2 = 8 \text{ min}$$
$$\vdots = \vdots \text{ min}$$

The exercise at constant HR of total duration $T_N=N$ 4 min is thus intended as composed of 4 minutes-phases (being juxtaposed excepting for 1 minute (or more)-ramp-phases connecting phases at constant reference HRs). It is clear that the choice of 4 minutes is not so stringent: any duration greater than 4 minutes is allowed, since here 4 minutes is the minimum duration required by any meaningful short term evaluation of HRV. Slight modifications of such parameter are thus allowed in accordance with the idea of the control algorithm. The phases may accordingly have a duration which varies from phase to phase.

Let us assume that, in each 4 minutes phase with acquisition at the time subsequence:

$$t_0^{[l]} = T_{l-1}, t_1^{[l]} = T_{l-1} + \frac{T_l - T_{l-1}}{n},$$

$$t_2^{[l]} = T_{l-1} + 2\frac{T_l - T_{l-1}}{n} \ldots , t_n^{[l]} = T_l$$

wherein l=1, 2, . . . , N, the inner control loop (for instance the HR control loop of the HR-controlled training/rehabilitation machine) is able to keep the HR for the i-subject constant and equal to the corresponding reference value (see for instance [8] and [10] for the cases of cycle-ergometers and treadmills). Let us introduce:

$$\alpha_\gamma > \beta_\gamma > 0$$

which are user-defined gains (taking for instance the values 0.1, 0.05, respectively) to be adapted to the specific set of healthy subjects or patients. Both of them will be used in the following to gradually characterize the possible increase (for instance 10%, 5%, as previously mentioned) of the HR reference values with respect to an initial HR reference sequence on the basis of the on-line monitored HRV indices.

Accordingly, let us preliminarily set an increasing sequence of HR reference values (such sequence can be, for instance, easily constructed from the available maximal HR and HR at rest or preliminarily provided to the user as a sub-result of the aforementioned threshold identification phase):

$$HR_{1,i}^* < HR_{2,i}^* < \ldots < HR_{N,i}^* \quad (6)$$

with $$HR_{1,i}^* > HR_{rest,i}$$

$$HR_{N,i}^* < HR_{maximal,i}$$

$$HR_{l,i}^* \geq (1+\alpha_\gamma) HR_{l-1,i}^*, \, l=2, \ldots, N$$

and such that:

$$\sum_{l=1}^{N} TRIMP(T_l) \leq S_{\Sigma, TRIMPi}$$

or $$\sum_{l=1}^{N} TRIMPi(T_l) \leq S_{\Sigma, TRIMPi}$$

(with both $TRIMP(T_l)$ and $TRIMPi(T_l)$ coinciding—excepting for the use of $B_i$, $C_i$—since being restrictively computed, from now on, on the basis of $HR_{l,i}^*$ in place of the corresponding $HR_{m,i}$ (for the phase l) and any $HR_i(t_j^{[l]})$, respectively, and with $S_{\Sigma, TRIMPi}$ being the given (individual or $\Sigma$-set-uniform, i.e. uniform for all individuals in the set $\Sigma$) TRIMP- or TRIMPi-cumulative upper bound for the i-th subject/patient). The last two inequalities thus fully characterize the TRIMP/TRIMPi compatibility of the given sequence of HR references.

A short term evaluated HRV index HRVi ("i" stands for index) for the i-th subject/patient is also available at the time instant values $T_1, \ldots, T_n$, which is computed, in HR constantly controlled stationary conditions and on the basis of the measured instants corresponding to the heart beats (as measured by standard devices/sensors), on the last 3 minutes of the 4 minutes (or more) time interval $[T_{l-1}, T_l]$ (l=1, 2, ..., N) (see for instance the spectral index LF/HF in [8] or in the following). As aforementioned, let $S_{\Sigma,HRV}$ be the HRVi (individual or set-uniform) threshold for the i-subject/patient and recall in the subsequent two conditions $\mathcal{A}$, B that, in the case of unavailability of lactate profiles—i.e., use of TRIMP in place of TRIMPi —, $B_i$ and $C_i$ become B and C.

Let us introduce two further user-defined gains:

$$\alpha_{HRV} > \beta_{HRV} > 1$$

(which may take for instance the values 2.5, and 2—to be adapted to the specific set of healthy subjects or patients—, respectively, and which will be used in the following to characterize the distance of the HRV index from the corresponding threshold), and define the quantity:

$$HR_{n,i,l+1,(\gamma_s)} = \frac{\gamma_s HR^*_{l+1,i} - HR_{rest,i}}{HR_{maximal,i} - HR_{rest,i}}$$

in terms of a positive real $\gamma_s$ and the conditions:

$\mathcal{A}$: $HRVi(T_l) \geq \alpha_{HRV} S_{\Sigma,HRV}$ and $$\sum_{k=1, k \neq l+1}^{N} TRIMPi(T_k) + 4\left[HR_{n,i,l+1,(1+\alpha_\gamma)} B_i e^{C_i HR_{n,i,l+1,(1+\alpha_\gamma)}}\right] \leq S_{\Sigma,TRIMPi}$$

wherein $$4\left[HR_{n,i,l+1,(1+\alpha_\gamma)} B_i e^{C_i HR_{n,i,l+1,(1+\alpha_\gamma)}}\right]$$

is the TRIMPi contribution resulting from the HR reference possibly modified through $\alpha_\gamma$ (so that the previous condition is still the condition concerning the TRIMPi compatibility corresponding to the candidate HR-reference adjustment);

$\mathcal{B}$: $HRVi(T_l) \geq \beta_{HRV} S_{\Sigma,HRV}$ and $$\sum_{k=1, k \neq l+1}^{N} TRIMPi(T_k) + 4\left[HR_{n,i,l+1,(1+\beta_\gamma)} B_i e^{C_i HR_{n,i,l+1,(1+\beta_\gamma)}}\right] \leq S_{\Sigma,TRIMPi}$$

wherein $4[HR_{n,i,l+1,(1+\beta_\gamma)} B_i e^{C_i HR_{n,i,l+1,(1+\beta_\gamma)}}]$ is the TRIMPi contribution resulting from the HR reference possibly modified through $\beta_\gamma$ (so that the previous condition is still the condition concerning the TRIMPi compatibility corresponding to the candidate HR-reference adjustment).

It is clear that the number 4 appearing in the preceding inequalities is related, without loss of generality, to the particular choice of a 4 minutes-long phase. We can substitute a parameter $V_1$ for any other duration greater than 4 minutes.

The recursive step for the algorithm generating the sequence of reference HRs is then as follows.

Step 1:
The algorithm provides the reference $HR_{1,i}^*$ to the first phase $[T_0, T_1]$ and modifies, for the phase $[T_l, T_{l+1}]$, l=1, 2, ..., N-1, the HR reference to $\gamma_l HR_{l+1,i}^*$ (renamed $HR_{l+1,i}^*$ after such modification) with:

$$\gamma_l = \max \begin{Bmatrix} 1 + \alpha_\gamma & \text{if } \mathcal{A} \\ 1 + \beta_\gamma & \text{if } \mathcal{B} \\ 1 & \text{otherwise} \end{Bmatrix}$$

only if, at each $T_l$ the condition:

$$HRVi(T_l) \leq S_{\Sigma,HRV}$$

does not hold; otherwise, a decrease of the HR reference to the previous value $HR_{l-1,i}^*$ (with $HR_{0,i}^*$ being intended as $HR_{rest,i}$) is performed.

The use of the upper bound $S_{\Sigma,TRIMPi}$ in conjunction with the user-defined gains $\alpha_\gamma, \beta_\gamma$ allows to define a well-defined scenario of possible choices for the HR references guaranteeing safe exercise operations for the i-th subject/patient. The sequence:

$$HR_{1,i}^* < HR_{2,i}^* < \ldots < HR_{N,i}^*$$

is thus only an initial safe estimate of the exercise demand, with the on-line ($\alpha_\gamma, \beta_\gamma$-based) safe adjustments on the basis of the short term evaluated HRV index HRVi (and its $\alpha_{HRV}$ and $\beta_{HRV}$-based distance from the related threshold) being performed to achieve the admissible "safe and effective dose" of exercise, on an individual and exercise moment-contingent basis, in order to maximize the individual health outcomes and to simultaneously reduce the possible risks of adverse (cardiac) events.

Figure 1:
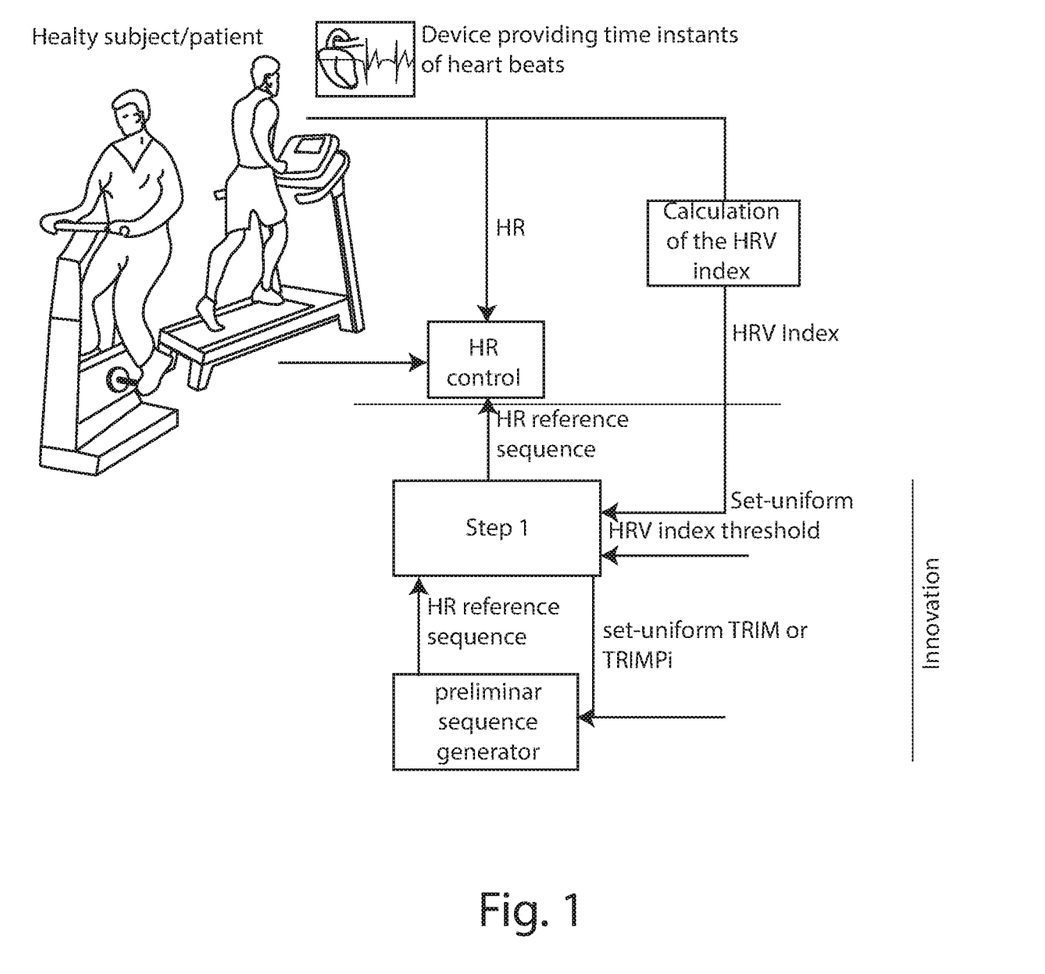
FIG. 1, showing the general structure of the invention (with visual reference to cycle-ergometers/treadmills).

The structure of the innovative tool is depicted in FIG. 1 (with specific reference to cycle-ergometers and treadmills).
Cycle Medical Personal Trainer (CMPT) Prototype To better explain the above methodology and its real application we provide FIGS. 2 and 3 concerning the results obtained by the CMPT prototype realized by the Applicant in order to show the feasibility of the above invention.

The technological maturity of such product is estimated by the TRL (Technology Readiness Level) at level 5, since the prototype system has been constructed and already tested in a relevant environment. The prototype has been realized by modifying the commercial DKN AM-5 through a Microchip PIC24FJ64GA004 microcontroller and by including a user-friendly Matlab interface (see the related FIGS. 2 and 3) along with a Matlab analysis code. The HR regulation control is a slight modification of the one presented in [8]—that also includes the motor dynamics into the control design and guarantees satisfactory HR regulation performance. The parameters used by the MPT are reported in FIG. 2 (the remaining ones take the corresponding aforementioned values). The pedalling speed in close to 50 rpm. The RR data are pre-filtered in order to remove the heart rate detection errors as well as to remove the linear trend. Indices coming from both time-domain and frequency-domain analysis are on-line computed. In particular, as an example, both parametric and non-parametric techniques are used to estimate the power spectral density of the filtered RR signal, with the use of: i) a cubic-spline interpolation and resampling for the RR signal and of the Welch's periodogram method in the non-parametric technique; ii) the Burg's method for the estimate of the autoregressive model coefficients in the parametric one.

Figure 2:
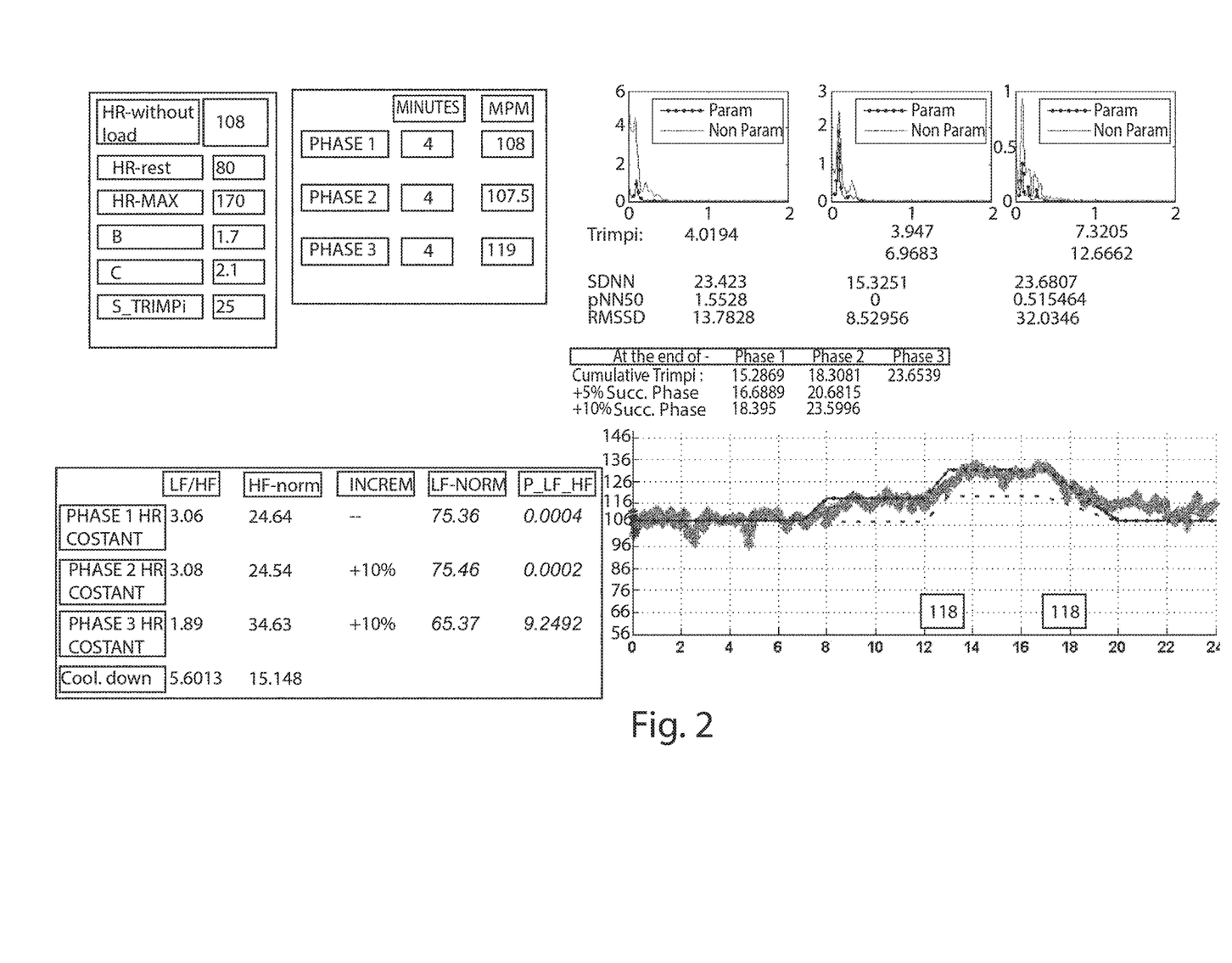
FIG. 2, showing an exemplary screenshot of a prototype of the program according to the invention, wherein input parameters for the TRIMPi computation are shown, along with:
  the HR values of the individual (thicker curve);
  the HR reference values for the different phases (dashed step curve in the graph below);
  the updated HR reference values for each phase (continuous step curve in the graph below);
  the HRV indices computed at each phase.

In FIG. 2 we accordingly recognize three main phases.
The first phase concerns the time interval [3 min, 7 min]: the HR of the user is regulated to the HR reference (108 bpm) computed in the phase 0 [0 min, 3 min] corresponding to the zero work load. This phase 1 also gives an initial value for the HRV index LF/HF (3.06) and for the HRV index HF-norm (24.64).

The second phase concerns the time interval [8 min, 12 min]: the HR reference has been a priori set to 107.5 bpm (it is slightly smaller than the HR reference value of the first phase since a so high value of the HR in phase 0 was not expected) and being left free to be changed by the algorithm.

The third phase concerns the time interval [13 min, 17 min]: the HR reference has been a priori set to 119 bpm being left free to be changed by the algorithm.

The initial sequence of HR reference values is thus represented by: 108 bpm, 107.5 bpm, 119 bpm. The exercise is TRIMPi-compatible (the related threshold is 25, while the constants B and C for the specific subject are 1.7 and 2.1, with the HR at rest and the maximal HR being equal to 80 and 170, respectively).

The HRV indices are computed on-line on the basis of the measured instants corresponding to the heart beats (as measured with standard devices/sensors), on the last 3 minutes of the 4 minutes-long phases at constant HR.

A 10% increase of the original HR reference is always applied to phases 2 and 3 since in such phases the HRV indices LF/HF (3.06, 3.08) are always greater than 2.5*1, where 1 is the threshold for the LF/HF characterizing the admissible nature of the exercise.

The definite new sequence of HR reference values is: 108 bpm, 118 bpm, 131 bpm. This sequence has been checked—at each step—to be TRIMPi-compatible (see again FIG. 2 reporting each HR-reference contribution to the TRIMPi).

A cooling-down phase recovering the HR corresponding to the zero work load ([20 min, 24 min]) is the last phase of the exercise at constant HR (108 bpm corresponding to the one identified in phase 0), showing a definite final increase of the LF/HF to 5.6013 and a definite final decrease of HF-norm to 15.148.

Figure 3:
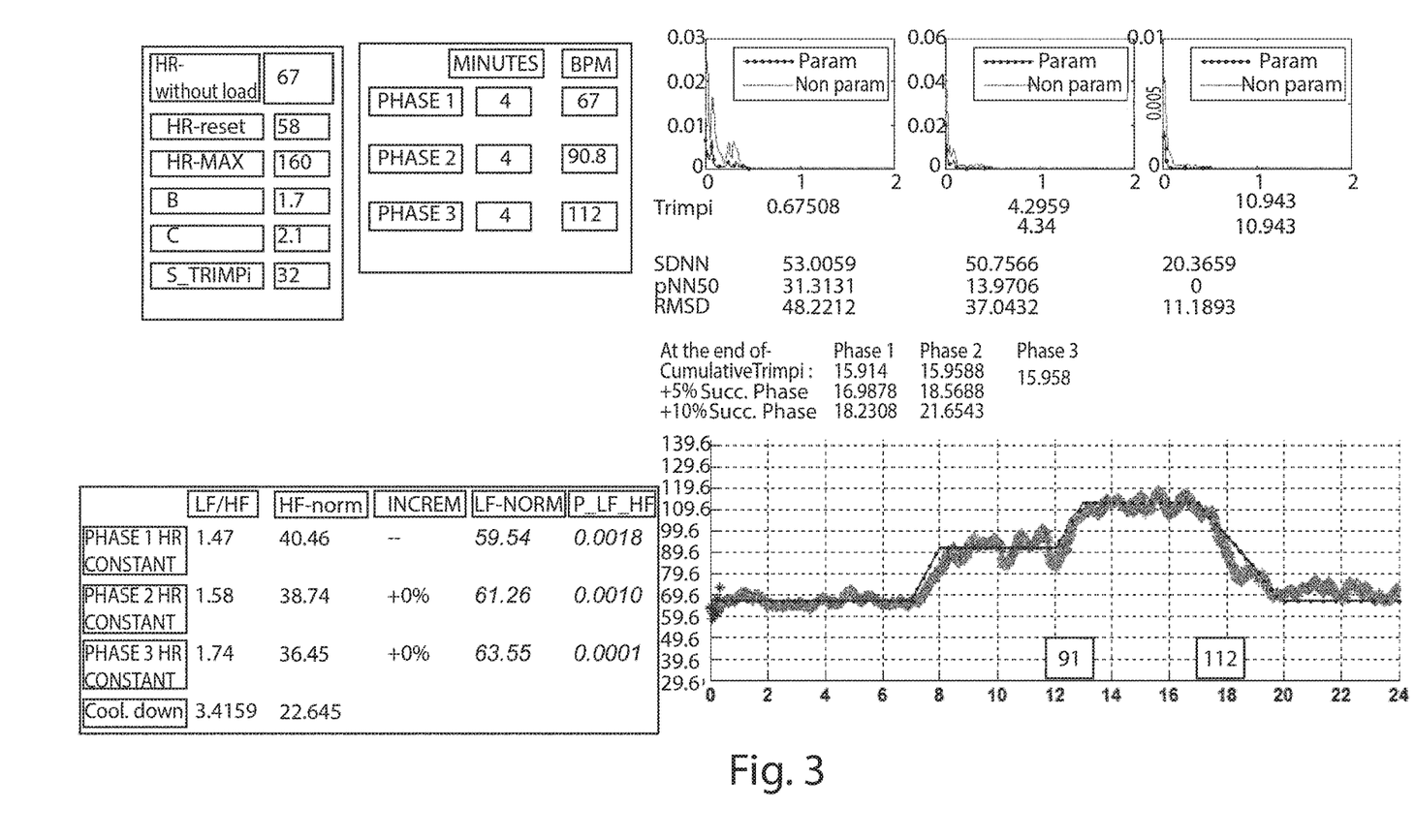
FIG. 3, showing an example similar to that of FIG. 2, wherein the dashed step curve practically coincides with the continuous step curve, what means that there was no substantial effort-increase in the training of the individual being allowed by the computed HRV indices.

FIG. 3 concerning another subject confirms the aforementioned overall strategy. No increase of the TRIMPi-compatible initial sequence of HR reference values (67 bpm, 90.8 bpm, 112 bpm) is carried out by the algorithm since the LF/HF values in phases 1 and 2 (1.47 and 1.58 being larger than 1 and smaller than 2*1 and 2.5*1) only allow the a priori established HR reference values 90.8 bpm and 112 bpm to be maintained.

Final reports concerning the complete HRV analysis performed during the exercise can be also provided, along with a detailed graph of the work load imposed by the cycle-ergometer to guarantee the regulation of the HR to the resulting reference values. They allow to establish an overall performance and training/rehabilitation status index. Finally we notice that the algorithm also provides an intuitively understandable visual feedback reported to the user corresponding to the 4 possible scenarios (very good: 10% increase; good: 5% increase; sufficiently good: 0% increase; attention please: decrease to the previous HR reference).

Short Description of the New Concept and Advantages
New Concept of the Invention The invention exercise training and rehabilitation method and apparatus is new, turnkey, completely automated, individually-tailored. It monitors the state of the user's cardiac regulation by the autonomic nervous system during each constant-HR-controlled exercise phase and then automatically provides the user's HR-level, for the subsequent HR-constant exercise phase, based on on-the-fly monitored HRV and on-the-fly calculated TRIMP or TRIMPi. A real-time adaptation of the exercise is thus individually performed during the exercise itself, and not only before the whole exercise execution as it happens for the competitor concepts and products in the actual market. The construction of remote communication medical databases collecting the data coming from the use of the new method also leads to the definition of a common application, analysis and evaluation scenario for both therapeutic evaluation and research purposes.

In particular, the data stored during the exercise can be used:
- as markers of long-term improvements;
- as markers of the advanced training effectiveness or for the rehabilitation therapy efficacy;
- for a posteriori confirmation of the possibility of clustering (at the level of the specific disease) and sub-clustering (at the level of the specific severity degree of the specific disease) the patients affected by chronic diseases;
- to definitely assess the effects of specific drug therapies in conjunction with the effects of exercise in chronic invalidating diseases.

A key feature of the invention method is the on-line (on-the-fly) adjustment of the exercise intensity (in terms of HR) for the specific individual subject/patient by integrating, in contrast to [13], [14] (including patents quoted therein) and [15], the TRIMP method—or TRIMPi method when available—with the on-line analysis of HRV indices restrictively evaluated during phases—with e.g. equal duration V of at least 4 minutes—at constant controlled HR (in which the HRV evaluation is actually effective).

Effects

The invention method and apparatus will allow each user to perform an individually-based training or rehabilitation program not restrictively based on pre-intervention criteria [6], such as the ones using simple HR-based methods (with the inherent above mentioned limitations).

The individual training is based, according to the invention, on target training load (as controlled by a traditional or future control unit/device programmed according to the invention) guided by the current variations in heart rate autonomic control within each given constant-HR-controlled exercise phase (with a consequently batch-continuous updating of training/rehabilitation load over time according to modifications that occur as training/rehabilitation progresses).

This is actually possible by simply using a low-cost, wearable and comfortable heart rate monitor (sensor strap) providing an impulse in correspondence to each heart beat.

Quantifying the suitable dose of exercise training load on an individual basis is therefore expected to provide the best way for improving health and rehabilitation status in both healthy subjects and patients with chronic diseases. Specific components of the ANS are thus assessed through the above HRV analysis and used as feedback signals that directly modulate the HR reference on individual and moment-contingent basis in order to avoid the passage from an admissible "safe and effective" operating condition to a non-admissible "less safe and partially effective" one. Hence, the invention realizes a step from controlling the target variable, i.e., the HR, to controlling the physiological determinants of the target variable during the exercise itself.

The invention method—in an era in which physical activity in terms of "Sports for all" is strongly recommended—guarantees performance that are crucial but currently absent in the actual market of rehabilitation and physical fitness. Such a new technique innovatively changes the current perspective of rehabilitation and training exercise (especially for fragile categories of subjects/patients), while vigorously moving toward the future of healthcare systems. It is aimed at improving health parameters and outcomes in patients affected by widely diffused chronic diseases (that have been shown to benefit from exercise training) as well as in healthy subjects (including elderly). In line with Industry 4.0, the new completely automated training/rehabilitation concept allows the inclusion of tele-monitoring systems directly allowing decisions to be decentralized and rehabilitation/training to be completely automatically performed in the (user-familiar) non-hospital setting. The aim of the present invention thus relies on overcoming the limits of the solutions according to the prior art and achieving the previously described technical results.

In summary, crucial advantages of the new method are:
improving the rehabilitation/training exercise effectiveness;
minimizing the related risks;
overcoming logistic problems for healthy subjects/patients;
generating a large amount of telemetry-acquired ready-to-use data in a "consistent" framework for both therapeutic evaluation and research purposes.

Applicative Scenarios

Some applications of the invention include:
a. Scenarios in which a batch-continuous adaptation of training/rehabilitation exercise prescription, in terms of volume and intensity, is needed for healthy subjects or patients with chronic diseases in order to maximize the health outcomes and/or reduce risks of adverse (cardiac) events.
b. Scenarios in which effectively practicing high-quality physical activity by healthy subjects or patients with chronic diseases is intended outside medically-supervised settings.
c. Scenarios in which a practical and user-friendly method of advanced training/rehabilitation exercise prescription for healthy subjects or patients with chronic diseases is mandatory, with performance/rehabilitation indices being accordingly defined.
d. Scenarios in which the effects of specific drug therapies in patients are to be comparatively assessed in conjunction with the effects of rehabilitation exercises.

In this respect, the rising burden of cardiovascular diseases across the globe drives the cardiac rehabilitation market. Factors boosting the cardiac rehabilitation market are rising geriatric population and increasing awareness about cardiovascular diseases. Interventions from government and international bodies such as the World Health Organization help to increase the level of awareness across the globe. Thus, increase in awareness level is expected to boost demand for rehabilitative products.

Even fitness market keeps on growing. Just as an example, according to the 2015 Europe Active European Health & Fitness Market report, the top ten players achieved total revenues of about EUR 2.8 billion in 2014. This represents 10.4% of the total European market, which has a market value of more than EUR 26.8 billion (+4%). For the sake of clearness, we can depict four specific applications of the proposed exercise training/rehabilitation conceptual methodology:

1) HR-controlled cycle-ergometers allowing for exercises at constant pedalling speed and at automatically regulated load (referred to as "CMPT: Cycle Medical Personal Trainer");
2) HR-controlled treadmills allowing for exercises at constant slope and at automatically regulated speed (referred to as "TMPT: Treadmill Medical Personal Trainer");
3) mobile phone application (app) with simple HR reference generator (referred to as "MPT: Medical Personal Trainer") for HR-controlled (by the device or by the user him/her-self) indoor or outdoor exercises;
4) mobile phone applications (apps) in tele-monitoring operations (referred to as "AMPT: Acoustic Medical Personal Trainer"), with acoustic indication to the user of the—remotely determined—optimal step frequency (in HR-controlled outdoor running exercises at constant ground slope) or pedalling frequency (in HR-controlled outdoor cycling exercises at constant ground slope) or simply with the indication of a batch non-invasive solely-HRV-based fatigue index to the user performing outdoor exercises (computed at each single training phase—of duration of at least 3 minutes automatically recognized to be at constant HR—) in order to have a ready-to-use tool to decide the modulation of future efforts.

The offer to the market of the possibly resulting technological products being generated by the present invention can be inflected in three different solutions (see the Tab below), with decreasing automation/individualization degree to satisfy all the users' desires and requirements from rehabilitation to advanced training. All of them are turnkey, affordable, ready-to-use solutions with hardware, software, tele-monitoring systems/services being all included in the package. Furthermore, the possibility of using personal accounts on a dedicated web-site can be included along with an on-line help service with quick responses to the user's questions.

| VERSION | EQUIPMENT | TARGET |
|---|---|---|
| Full-Equipment i-Version | CMPT or TMPT in tele-monitoring operation with TRIMPi constraint inclusion. | Rehabilitation centers; high-level fitness centres with medical figures involvement. |
| Full-Equipment Version | CMPT or TMPT in tele-monitoring operation with TRIMP constraint inclusion. | fitness centres with no medical figures involvement. |
| App version | MPT; AMPT; TRIMP inclusion; dedicated web-site with community generation. | Cycle-ergometer/treadmill manufacturers; professional users; general users. |

Improvements with Respect to Prior Art

Existing exercise training methods and apparatuses (including the ones described in [13]-[15]) are not thought and configured to provide the above features and advantages, since:

they do not adjust the exercise intensity on the basis of both TRIMP/TRIMPi and the on-line short term evaluated (on-the-fly) HRV whose indices are meaningfully computed during constant-HR-controlled phases;

they do not constitute a completely automated, individually-tailored ready-to-use solution (in the user-familiar setting for both patients with chronic diseases and healthy subjects) that is able to offer, in a "consistent" framework to be used for therapeutic and research purposes, remote information on the time-course profile of the on-line adaptations to rehabilitation/training.

REFERENCES

[1] Case M A, Burwick H A, Volpp K G, Patel M S. Accuracy of smartphone applications and wearable devices for tracking physical activity data. *JAMA (The Journal of the American Medical Association)* 2015; 313:625-626.
[2] Cottin F, Médique C, Lepêtre P M, Papelier Y, Koralsztein J P, Billat V. Heart rate variability during exercise performed below and above ventilatory threshold. *Medicine and Science in Sports and Exercise* 2004; 36(4):594-600.
[3] D'Souza A, Bucchi A, Johnsen A B, Logantha S J, Monfredi O, Yanni J, Prehar S, Hart G, Cartwright E, Wisloff U, Dobryznski H, DiFrancesco D, Morris G M, Boyett M R. Exercise training reduces resting heart rate via downregulation of the funny channel HCN4. *Naure-Communications* 2014; 5:3775.
[4] Iellamo F, Manzi V, Caminiti G, Sposato B, Massaro M, Cerrito A, Rosano G, Volterrani M. Dose-response relationship of baroreflex sensitivity and heart rate variability to individually-tailored exercise training in patients with heart failure. *International Journal of Cardiology* 2013; 166:334-339.
[5] Manzi V, Castagna C, Padua E, Lombardo M, D'Ottavio S, Massaro M, Volterrani M., Iellamo F. Dose-response relationship of autonomic nervous system responses to individualized training impulse in marathon runners. *American Journal of Physiology—Heart and Circulatory Physiology*, 2009; 296(6):H1733-H1740.
[6] Kiviniemi A. M., Hautala A. J., Kinnunen H., Tulppo M. P. Endurance training guided individually by daily heart rate variability measurements. *European Journal of Applied Physiology* 2007; 101:743-751.
[7] Kokkinos P, Myers J. Exercise and physical activity. Clinical outcomes and applications. *Circulation* 2010; 122:1637-1648.
[8] Paradiso M, Pietrosanti S, Scalzi S, Tomei P, Verrelli C M. Experimental heart rate regulation in cycle-ergometer exercises. *IEEE Transactions on Biomedical Engineering* 2013; 60(1):135-139.
[9] Physical Activity Guidelines Advisory Committee. *Physical Activity Guidelines Advisory Committee Report,* 2008. Washington, D.C.: U.S. Department of Health and Human Services, 2008.
[10] Scalzi S, Tomei P, Verrelli C M. Nonlinear control techniques for the heart rate regulation in treadmill exercises. *IEEE Transactions on Biomedical Engineering* 2012; 59(3):599-603.
[11] Shiroma E J, Lee I M. Physical activity and cardiovascular health. Lessons learned from epidemiological studies across age, gender, and race/ethnicity. *Circulation* 2010; 122:743-752.
[12] Manzi V, Iellamo F, Impellizzeri F, D'Ottavio S, Castagna C. Relation between individualized training impulses and performance in distance runners. Medicine & Science in Sports & Exercise, 2009; 41(11): 2090-2096.
[13] US 2015/217164 A1 (LAGREE SEBASTIEN ANTHONY LOUIS [US]) 6 Aug. 2015.
[14] WO 2007/099206 (FIRSTBEAT TECHNOLOGIES OY [FI]; KURUNMAEKI VELI-PEKKA [FI]; SAALASTI S) 7 Sep. 2007.
[15] US 2011/207110 A1 (HUOVINEN KUKKA [FI] 25 Aug. 2011.

The present invention was disclosed for illustrative, non-limitative purposes, according to preferred embodiments thereof, but it has to be understood that any variations and/or modifications can be made by the persons skilled in the art without for this reason escaping from the relative scope of protection, as defined in the enclosed claims.

The invention claimed is:

1. An exercise session training and/or rehabilitation method, comprising:
   providing a heart beats measuring means for and connected to each individual i belonging to a set $\Sigma$ of I individuals, with I denoting an integer greater than 1 and with the heart beats measuring means being able to provide a time-sequence of impulses corresponding to each heart beat, wherefrom heart rate HR and heart rate variability HRV are calculated;
   providing each individual i of the set $\Sigma$ with: a training/rehabilitation device comprising heart rate (HR) control configured to tune an effort load provided by the training/rehabilitation device for the individual i; and
   providing each training/rehabilitation device with microcontroller for controlling said HR control, said microcontroller being connected to said HR control;
   wherein the following steps are executed by a respective said microcontroller for each individual i:
   subdividing an exercise session of total duration T, depending on each individual, into N subsequent session phases at a constant HR reference value, wherein N is a positive integer and where the session phases start at correspondingly subsequent time instants $T_0$, $T_1$, ... $T_{N-1}$;
   assigning to each of said session phases, a respective pre-defined HR reference value from a sequence of HR reference values: $HR_{1,i}^* < HR_{2,i}^* < \ldots < HR_{N,i}^*$ with $HR_{1,i}^* > HR_{rest,i}$ and $HR_{N,i}^* < HR_{maximal,i}$; and
   modifying, for each session phase $[T_l, T_{l+1}]$, l=1, 2, ..., N-1, the pre-defined HR reference value of said sequence of HR reference values to $\gamma_l HR_{l+1,i}^*$, renamed $HR_{l+1,i}^*$ after the modification;
   wherein the HR control is concurrently configured to maintain a HR profile of each individual within 5% of said modified sequence of HR reference values $HR_{1,i}^* < HR_{2,i}^* < \ldots < HR_{N,i}^*$ wherein
   $HR_{rest,i}$ is a pre-determined HR at rest for the individual i,
   $HR_{maximal,i}$ is a pre-defined maximal HR for the individual i,
   $\gamma_l$ is a real positive number that is determined, for l=1, 2, ..., N-1, on the basis of:
   a HRV index $HRVi(T_l)$ for the individual i, as calculated on the basis of the heart beats time-sequence during a last portion of a preceding session phase $[T_{l-1}, T_l]$; and
   an individualized TRainingIMPulse value termed TRIMPi or TRainingIMPulse value termed TRIMP for the individual i, as calculated on the basis of:
   the aforementioned pre-defined HR reference values;
   durations $V_l = T_{l+1} - T_l$ of all the session phases $[T_l, T_{l+1}]$, l=0, 1, 2, ..., N-1,
   the HR at rest $HR_{rest,i}$ for the individual i, and
   the maximal HR $HR_{maximal,i}$ for the individual i.

2. The method according to claim 1, wherein each phase duration $V_l$, l=0, 1, 2, ..., N-1, is equal to 4 minutes.

3. The method according to claim 2, wherein the last portion of each phase $[T_{l-1}, T_l]$, l=1, 2, ..., N-1—that is used to compute the HRV index HRVi—is at least 3-minutes-long.

4. The method according to claim 1, wherein said pre-defined HR reference values $HR_{1,i}^* < HR_{2,i}^* < \ldots < HR_{N,i}^*$ is TRIMP- or TRIMPi-compatible, namely $$\sum_{k=1}^{N} TRIMPi(T_k) \leq S_{\Sigma,TRIMPi}$$

with $S_{\Sigma,TRIMPi}$ denoting a pre-defined individual or set-uniform threshold for a cumulative TRIMPi or TRIMP value.

5. The method according to claim 1, wherein, if the HRV index $HRVi(T_l) \leq S_{\Sigma,HRV}$, then $\gamma_l < 1$, otherwise $\gamma_l \geq 1$, wherein $S_{\Sigma,HRV}$ is a pre-defined individual or set-uniform threshold so that the HRV index $HRVi(T_l)$ larger than $S_{\Sigma,HRV}$ identifies admissible exercises and the HRV index $HRVi(T_l)$ smaller than or equal to $S_{\Sigma,HRV}$ identifies non-admissible exercises.

6. The method according to claim 1, wherein $\gamma_l$ is determined as follows:

$$\gamma_l = \max\begin{cases} 1 + \alpha_\gamma & \text{if } \mathcal{A} \\ 1 + \beta_\gamma & \text{if } \mathcal{B} \\ 1 & \text{otherwise} \end{cases}$$

wherein:

$\alpha_\gamma, \beta_\gamma$ are pre-defined user-defined gains with $\alpha_\gamma > \beta_\gamma > 0$ and $HR_{l,i}^* \geq (1+\alpha_\gamma)HR_{l-1,i}^*$, $l=2, \ldots, N$ $\mathcal{A}$ is the double condition:

$HRVi(T_l) \geq \alpha_{HRV} S_{\Sigma,HRV}$ in which $\alpha_{HRV}$ is a user-defined gain, and $$\sum_{k=1, k \neq l+1}^{N} TRIMPi(T_k) + V_l \left[ HR_{n,i,l+1(1+\alpha_\gamma)} B_i e^{C_i HR_{n,i,l+1,(1+\alpha_\gamma)}} \right] \leq S_{\Sigma,TRIMPi}$$

wherein $B_i$ and $C_i$ are pre-defined constants variable for each individual i in the TRIMPi, while they are equal for any individual in the case of TRIMP, subscript "n" stands for "normalized", and $HR_{n,i,l+1,(1+\alpha_\gamma)}$ is:

$$HR_{n,i,l+1(1+\alpha_\gamma)} = \frac{(1+\alpha_\gamma)HR_{l+1,i}^* - HR_{rest,i}}{HR_{maximal,i} - HR_{rest,i}};$$

$\mathcal{B}$ is the double condition:

$HRVi(T_l) \geq \beta_{HRV} S_{\Sigma,HRV}$ wherein $\beta_{HRV}$ is a further pre-defined gain with $\alpha_{HRV} > \beta_{HRV} > 1$, and $$\sum_{k=1, k \neq l+1}^{N} TRIMPi(T_k) + V_l \left[ HR_{n,i,l+1(1+\beta_\gamma)} B_i e^{C_i HR_{n,i,l+1,(1+\beta_\gamma)}} \right] \leq S_{\Sigma,TRIMPi}$$

in which $HR_{n,i,l+1,(1+\beta_\gamma)}$ is:

$$HR_{n,i,l+1(1+\beta_\gamma)} = \frac{(1+\beta_\gamma)HR_{l+1,i}^* - HR_{rest,i}}{HR_{maximal,i} - HR_{rest,i}};$$

the above determination of $\gamma_l$ holds true only if, at each $T_l$, the condition:

$HRVi(T_l) \leq S_{\Sigma,HRV}$ does not hold; otherwise, a decrease of the HR reference to the previous value $HR_{l-1,i}^*$ is carried out, with $HR_{0,i}^* = HR_{rest,i}$.

7. The method according to claim 1, wherein, with $l=0, 1, \ldots, N-1$:

$$TRIMPi(T_{l+1}) = V_l [HR_{n,i,l+1,(1)} B_i e^{C_i HR_{n,i,l+1,(1)}}]$$

and:

$$HR_{n,i,l+1,(1)} = \frac{HR_{l+1,i}^* - HR_{rest,i}}{HR_{maximal,i} - HR_{rest,i}}.$$

8. The method according to claim 1, wherein the HR control is concurrently configured to maintain the HR profile of each individual within 3% of said modified sequence of HR reference values.

9. Individually tailored exercise session training and rehabilitation apparatus, comprising:
heart beats measuring means for measuring time-sequence of impulses corresponding to each heart beat of an individual i belonging to a set of I individuals, with I denoting an integer greater than 1;
a training/rehabilitation device for each individual of the aforementioned set of individuals,
wherein the training/rehabilitation device has:
HR control configured to tune an effort load provided by the training/rehabilitation device for the individual i; and
microcontroller for controlling said HR control, said microcontroller being connected to said HR control and configured to execute the following steps:
subdividing an exercise session of total duration T, depending on each individual, into N subsequent session phases at a constant HR reference value, wherein N is a positive integer and where the session phases start at correspondingly subsequent time instants $T_0$, $T_1, \ldots T_{N-1}$;
assigning to each of said session phases, a respective pre-defined HR reference value from a sequence of HR reference values: $HR_{1,i}^* < HR_{2,i}^* < \ldots < HR_{N,i}^*$ with $HR_{1,i}^* > HR_{rest,i}$ and $HR_{N,i}^* < HR_{maximal,i}$; and
modifying, for each session phase $[T_l, T_{l+1}]$, $l=1, 2, \ldots, N-1$, the pre-defined HR reference value of said sequence of HR reference values to $\gamma_l HR_{l+1,i}^*$, renamed $HR_{l+1,i}^*$ after the modification;
wherein the HR control is concurrently configured to maintain a HR profile of each individual within 5% of said modified sequence of HR reference values $HR_{1,i}^* < HR_{2,i}^* < \ldots < HR_{N,i}^*$, wherein
$HR_{rest,i}$ is a pre-determined HR at rest for the individual i,
$HR_{maximal,i}$ is a pre-defined maximal HR for the individual i,
$\gamma_l$ is a real positive number that is determined, for $l=1, 2, \ldots, N-1$, on the basis of:
a HRV index $HRVi(T_l)$ for the individual i, as calculated on the basis of the heart beats time-sequence during a last portion of a preceding session phase $[T_{l-1}, T_l]$; and
an individualized TRainingIMPulse value termed TRIMPi or TRainingIMPulse value termed TRIMP for the individual i, as calculated on the basis of:
the aforementioned pre-defined HR reference values;
durations $V_l = T_{l+1} - T_l$ of all the session phases $[T_l, T_{l+1}]$, $l=0, 1, 2, \ldots, N-1$,
the HR at rest $HR_{rest,i}$ for the individual i, and
the maximal HR $HR_{maximal,i}$ for the individual i.

* * * * *